US007928410B2

(12) United States Patent
Ose et al.

(10) Patent No.: US 7,928,410 B2
(45) Date of Patent: Apr. 19, 2011

(54) OPTICAL BEAM POINTING SYSTEM FOR SETTING IRRADIATION POSITION FOR RADIATION

(75) Inventors: Masuo Ose, Kyoto (JP); Hajime Fujita, Kyoto (JP); Kuniyuki Miyashita, Osaka (JP); Yosifumi Fujikawa, Shiga (JP)

(73) Assignees: Takenaka System Co., Ltd., Kyoto (JP); Takenaka Optonic Co., Ltd., Kyoto (JP)

( * ) Notice: Subject to any disclaimer, the term of this patent is extended or adjusted under 35 U.S.C. 154(b) by 303 days.

(21) Appl. No.: 12/270,050

(22) Filed: Nov. 13, 2008

(65) Prior Publication Data
US 2009/0140171 A1 Jun. 4, 2009

(30) Foreign Application Priority Data
Nov. 29, 2007 (JP) .................. 2007-309001

(51) Int. Cl.
G01N 23/00 (2006.01)
(52) U.S. Cl. .................. 250/491.1; 250/492.1; 600/426
(58) Field of Classification Search ............... 250/491.1
See application file for complete search history.

(56) References Cited

U.S. PATENT DOCUMENTS

| 4,223,227 | A | * | 9/1980 | Horwitz | 378/206 |
| 5,651,043 | A | * | 7/1997 | Tsuyuki et al. | 378/65 |
| 5,684,578 | A | | 11/1997 | Nower et al. | |
| 6,405,072 | B1 | * | 6/2002 | Cosman | 600/426 |
| 6,486,457 | B1 | * | 11/2002 | Dorsel et al. | 250/201.4 |
| 7,230,964 | B2 | * | 6/2007 | Das et al. | 372/55 |
| 2007/0041692 | A1 | * | 2/2007 | Yang | 385/134 |
| 2007/0291267 | A1 | | 12/2007 | Rockseisen | |

FOREIGN PATENT DOCUMENTS

| EP | 1870134 A1 | 12/2007 |
| GB | 2331360 A | 5/1999 |
| JP | 2006-122452 | 5/2006 |

OTHER PUBLICATIONS

Horwitz, Norman H., et al., "An instrument for aligning patient-positioning lasers", Medical Physics, Mar. 1, 1978, pp. 164-166, vol. 5, No. 1, AIP, Melville, NY, US.

* cited by examiner

Primary Examiner — Phillip A Johnston
(74) Attorney, Agent, or Firm — Hodgson Russ LLP

(57) ABSTRACT

An optical beam pointing system for setting an irradiation position and which is capable of automatically performing positional adjustments of visible light beams with respect to an aiming center. The system uses opposed pointers disposed on opposite sides of an irradiation center, each pointer including a light-projecting portion for projecting a beam aimed at the irradiation center, a light-receiving portion for generating a detection signal, and a control portion.

24 Claims, 8 Drawing Sheets

A

B

A

B

A

B

OPTICAL BEAM POINTING SYSTEM FOR SETTING IRRADIATION POSITION FOR RADIATION

CROSS-REFERENCE TO RELATED APPLICATIONS

This application claims priority of Japanese Patent Application No. 2007-309001, filed Nov. 29, 2007, the disclosure of which is incorporated herein by reference.

BACKGROUND OF THE INVENTION

1. Field of the Invention

The present invention relates to an optical beam pointing system for pointing an irradiation center for radiation when positioning an irradiation target at the irradiation center.

2. Description of the Background Art

Conventionally, radiation therapy is performed by a radiation therapy apparatus, such as a linac (linear accelerator), which irradiates patient lesions with radiation multiple times, thereby destroying abnormal cells, such as cancer cells, while maintaining normal cells.

Before performing radiation therapy, a lesion in a body is located based on diagnostic imaging, such as CT scanning, and the size and range of a radiation target is determined. After the determination, marks for indicating the position to be irradiated with radiation are made on the skin of the patient in order to eliminate the necessity of locating the position to be irradiated with radiation in each irradiation. Normally, there are three marks made by an ink pen or suchlike on the front, left, and right sides of the patient.

For example, as shown in FIG. 13 of Japanese Laid-Open Patent Publication No. 2006-122452, a radiation therapy room is equipped with a radiation therapy apparatus, and three optical beam pointers 93, 94, and 95 disposed in the vicinity of the radiation therapy apparatus, one being on the front side of a patient M laid on a bed 91, the others being disposed in opposition to each other on the left and right sides of the patient. Each of the optical beam pointers 93, 94, and 95 points the irradiation center (aiming center) for the radiation therapy apparatus by projecting a visible light beam passing through the irradiation center.

The patient is positioned such that the irradiation centers pointed by the optical beam pointers are aligned with the irradiation position for radiation, i.e., the visible light beams from the optical beam pointers are respectively incident on the three marks made on the skin of the patient.

As described above, the visible light beams from the optical beam pointers are set so as to pass through the irradiation center for the radiation therapy apparatus. However, in some cases, the visible light beams from the optical beam pointers miss the irradiation center due to some factor such as facility aging or variations in atmospheric conditions. In each such case, maintenance workers have to adjust the projection angles of the optical beam pointers, forcing them to perform troublesome work.

Also, such adjustments require extraordinary subtlety, and therefore may vary from one maintenance worker to another.

SUMMARY OF THE INVENTION

The present invention has been made in view of the above circumstances, and an objective thereof is to provide an optical beam pointing system for setting the irradiation position for radiation, which is capable of automatically performing positional adjustments of visible light beams with respect to an aiming center without requiring any maintenance worker.

To solve the above problem, the present invention provides (1) an optical beam pointing system for setting an irradiation position for radiation, the system pointing an irradiation center for radiation when positioning an irradiation target at the irradiation center, comprising: first and second optical beam pointers disposed on opposite sides of the irradiation center and opposed each other, wherein, the first optical beam pointer includes a first light-projecting portion for projecting a first visible light beam aimed at the irradiation center, the second optical beam pointer includes a second light-projecting portion for projecting a second visible light beam aimed at the irradiation center, the first optical beam pointer includes a first light-receiving portion for receiving the second visible light beam and generating a first detection signal in accordance with a receiving position at which the second visible light beam is received, the second optical beam pointer includes a second light-receiving portion for receiving the first visible light beam and generating a second detection signal in accordance with a receiving position at which the first visible light beam is received, the first optical beam pointer includes a first control portion having previously stored therein, as a first reference value, a value for the first detection signal to be generated by the first light-receiving portion which has received the second visible light beam passing through the irradiation center as aimed, the first control portion generating a first correction signal for correcting a projection angle of the second light-projecting portion when a difference between the first reference value and a value for the first detection signal actually generated by the first light-receiving portion falls outside a tolerable range, the second optical beam pointer includes a second control portion having previously stored therein, as a second reference value, a value for the second detection signal to be generated by the second light-receiving portion which has received the first visible light beam passing through the irradiation center as aimed, the second control portion generating a second correction signal for correcting a projection angle of the first light-projecting portion when a difference between the second reference value and a value for the second detection signal actually generated by the second light-receiving portion falls outside a tolerable range, the first optical beam pointer includes a first transmitting portion for transmitting the first correction signal to the second optical beam pointer, the second optical beam pointer includes a second transmitting portion for transmitting the second correction signal to the first optical beam pointer, the first optical beam pointer includes a first receiving portion for receiving the second correction signal from the second transmitting portion, the second optical beam pointer includes a second receiving portion for receiving the first correction signal from the first transmitting portion, the first optical beam pointer includes a first actuator for correcting a projection angle of the first light-projecting portion in accordance with the second correction signal received by the first receiving portion, such that the first visible light beam passes through the irradiation center, and the second optical beam pointer includes a second actuator for correcting a projection angle of the second light-projecting portion in accordance with the first correction signal received by the second receiving portion, such that the second visible light beam passes through the irradiation center.

In addition, the present invention provides (2) the optical beam pointing system with the above configuration, wherein, the first optical beam pointer further includes a first interface portion, the first control portion is adapted to store, as the first reference value, the first detection signal generated by the first light-receiving portion when the first interface portion receives a user's first setting operation, the second optical beam pointer further includes a second interface portion, and the second control portion is adapted to store, as the second reference value, the second detection signal generated by the second light-receiving portion when the second interface portion receives a user's second setting operation.

In addition, the present invention provides (3) an optical beam pointing system for setting an irradiation position for radiation, the system pointing an irradiation center for radiation when positioning an irradiation target at the irradiation center, comprising: first and second optical beam pointers disposed on opposite sides of the irradiation center and opposed each other, wherein, the first optical beam pointer includes a first light-projecting portion for projecting a first visible light beam aimed at the irradiation center, the second optical beam pointer includes a second light-projecting portion for projecting a second visible light beam aimed at the irradiation center, the first optical beam pointer includes a first light-receiving portion for receiving the second visible light beam and generating a first detection signal in accordance with a receiving position at which the second visible light beam is received, the second optical beam pointer includes a second light-receiving portion for receiving the first visible light beam and generating a second detection signal in accordance with a receiving position at which the first visible light beam is received, the first optical beam pointer includes a first transmitting portion for transmitting the first detection signal to the second optical beam pointer, the second optical beam pointer includes a second transmitting portion for transmitting the second detection signal to the first optical beam pointer, the first optical beam pointer includes a first receiving portion for receiving the second detection signal from the second transmitting portion, the second optical beam pointer includes a second receiving portion for receiving the first detection signal from the first transmitting portion, the first optical beam pointer includes a first control portion having previously stored therein, as a second reference value, a value for the second detection signal to be generated by the second light-receiving portion which has received the first visible light beam passing through the irradiation center as aimed, the first control portion generating a second correction signal for correcting a projection angle of the first light-projecting portion when a difference between the second reference value and a value for the second detection signal received by the first receiving portion falls outside a tolerable range, the second optical beam pointer includes a second control portion having previously stored therein, as a first reference value, a value for the first detection signal to be generated by the first light-receiving portion which has received the second visible light beam passing through the irradiation center as aimed, the second control portion generating a first correction signal for correcting a projection angle of the second light-projecting portion when a difference between the first reference value and a value for the first detection signal received by the second receiving portion falls outside a tolerable range, the first optical beam pointer includes a first actuator for correcting a projection angle of the first light-projecting portion in accordance with the second correction signal, such that the first visible light beam passes through the irradiation center, and the second optical beam pointer includes a second actuator for correcting a projection angle of the second light-projecting portion in accordance with the first correction signal, such that the second visible light beam passes through the irradiation center.

In addition, the present invention provides (4) the optical beam pointing system with the above configuration (3), wherein, the first optical beam pointer further includes a first interface portion, the first control portion transmits a first instruction signal to the second receiving portion via the first transmitting portion when the first interface portion receives a user's first setting operation, the second control portion is adapted to store, as the first reference value, the first detection signal received by the second receiving portion when the second control portion receives the first instruction signal via the second receiving portion, the second optical beam pointer further includes a second interface portion, the second control portion transmits a second instruction signal to the first receiving portion via the second transmitting portion when the second interface portion receives a user's second setting operation, and the first control portion is adapted to store, as the second reference value, the second detection signal received by the first receiving portion when the first control portion receives the second instruction signal via the first receiving portion.

In addition, the present invention provides (5) the optical beam pointing system with any of the above configurations 1 to 4, wherein, the first light-projecting portion is adapted to project the first visible light beam in the shape of a cross consisting of a first vertical beam spreading vertically and a first horizontal beam spreading horizontally, the second light-projecting portion is adapted to project the second visible light beam in the shape of a cross consisting of a second vertical beam spreading vertically and a second horizontal beam spreading horizontally, the first light-receiving portion consists of two first optical receivers, one for receiving the second vertical beam, the other for receiving the second horizontal beam, and the second light-receiving portion consists of two second optical receivers, one for receiving the first vertical beam, the other for receiving the first horizontal beam.

In addition, the present invention provides (6) the optical beam pointing system with any of the above configurations 1 to 5, wherein each signal is wirelessly received/transmitted between the first transmitting portion and the second receiving portion and/or between the second transmitting portion and the first receiving portion.

In addition, the present invention provides (7) the optical beam pointing system with any of the above configurations 1 to 6, further comprising: a third optical beam pointer disposed above the irradiation center; and an optical beam monitoring device disposed laterally to the third optical beam pointer, wherein, the third optical beam pointer includes: a third light-projecting portion for projecting a third visible light beam aimed at the irradiation center; and a beam splitter for generating a fractional light beam from the third visible light beam, the fractional light beam traveling toward the optical beam monitoring device, the optical beam monitoring device includes: a third light-receiving portion for receiving the fractional light beam and generating a third detection signal in accordance with a receiving position at which the fractional light beam is received; a third control portion having previously stored therein, as a third reference value, a value for the third detection signal to be generated by the third light-receiving portion which has received the fractional light beam derived from the third visible light beam passing through the irradiation center as aimed, the third control portion generating a third correction signal for correcting a projection angle of the third light-projecting portion when a difference between the third reference value and a value for the third detection signal actually generated by the third light-receiving portion falls outside a tolerable range, and a third transmitting portion for transmitting the third correction signal to the third optical beam pointer, and the third optical beam pointer includes: a third receiving portion for receiving the third correction signal from the third transmitting portion; and a third actuator for correcting a projection angle of the third light-projecting portion in accordance with the third correction signal received by the third receiving portion, such that the third visible light beam passes through the irradiation center.

In addition, the present invention provides (8) the optical beam pointing system with the above configuration (7), wherein, the optical beam monitoring device further includes a third interface portion, and the third control portion is adapted to store, as the third reference value, the third detection signal generated by the third light-receiving portion when the third interface portion receives a user's third setting operation.

In addition, the present invention provides (9) the optical beam pointing system with any of the above configurations 1 to 6, further comprising: a third optical beam pointer disposed above the irradiation center; and an optical beam monitoring device disposed laterally to the third optical beam pointer, wherein, the third optical beam pointer includes: a third light-projecting portion for projecting a third visible light beam aimed at the irradiation center; and a beam splitter for generating a fractional light beam from the third visible light beam, the fractional light beam traveling toward the optical beam monitoring device, the optical beam monitoring device includes: a third light-receiving portion for receiving the fractional light beam and generating a third detection signal in accordance with a receiving position at which the fractional light beam is received; and a third transmitting portion for transmitting the third detection signal to the third optical beam pointer, and the third optical beam pointer includes: a third receiving portion for receiving the third detection signal from the third transmitting portion; a third control portion having previously stored therein, as a third reference value, a value for the third detection signal to be generated by the third light-receiving portion which has received the fractional light beam derived from the third visible light beam passing through the irradiation center as aimed, the third control portion generating a third correction signal for correcting a projection angle of the third light-projecting portion when a difference between the third reference value and a value for the third detection signal received by the third receiving portion falls outside a tolerable range; and a third actuator for correcting a projection angle of the third light-projecting portion in accordance with the third correction signal, such that the third visible light beam passes through the irradiation center.

In addition, the present invention provides (10) the optical beam pointing system with the above configuration (9), wherein, the optical beam monitoring device further includes: a third interface portion; and a fourth control portion electrically connected to at least the third interface portion and the third transmitting portion, the fourth control portion transmits a third instruction signal to the third receiving portion via the third transmitting portion when the third interface portion receives a user's third setting operation, and the third control portion is adapted to store, as the third reference value, the third detection signal received by the third receiving portion when the third control portion receives the third instruction signal via the third receiving portion.

In addition, the present invention provides (11) the optical beam pointing system with any of the configurations 7 to 10, wherein, the third light-projecting portion is adapted to project the third visible light beam traveling vertically in the shape of a cross consisting of a traversal beam spreading along the line connecting the first optical beam pointer and the second optical beam pointer, and a longitudinal beam spreading perpendicular to the traversal beam, the longitudinal beam is converted by the beam splitter into a third horizontal beam spreading horizontally, the third horizontal beam forming a part of the fractional light beam, the traversal beam is converted by the beam splitter into a third vertical beam spreading vertically, the third vertical beam forming the other part of the fractional light beam, the third optical beam pointer further includes a optical element for converting the third horizontal beam into a fourth vertical beam spreading vertically by rotating spread directions of the third horizontal beam by 90°, and the third light-receiving portion consists of two third optical receivers, one for receiving the third vertical beam, the other for receiving the fourth vertical beam.

In addition, the present invention provides (12) the optical beam pointing system with any of the above configurations 7 to 11, wherein each signal is wirelessly received/transmitted between the third transmitting portion and the third receiving portion.

In the optical beam pointing system configured as described above, the projection angle of each visible light beam is always automatically corrected while the visible light beam is being projected. Therefore, the optical beam pointing system according to the present invention makes it possible to always accurately point the irradiation center for radiation from the radiation therapy apparatus. In addition, maintenance workers do not have to adjust the projection angle of each visible light beam each time such an adjustment is required. In addition, there is no possibility of causing variations in projection angle adjustment among maintenance workers.

DESCRIPTION OF THE PREFERRED EMBODIMENTS

Hereinafter, a preferred embodiment of the present invention will be described with reference to the drawings.

Figure 1:
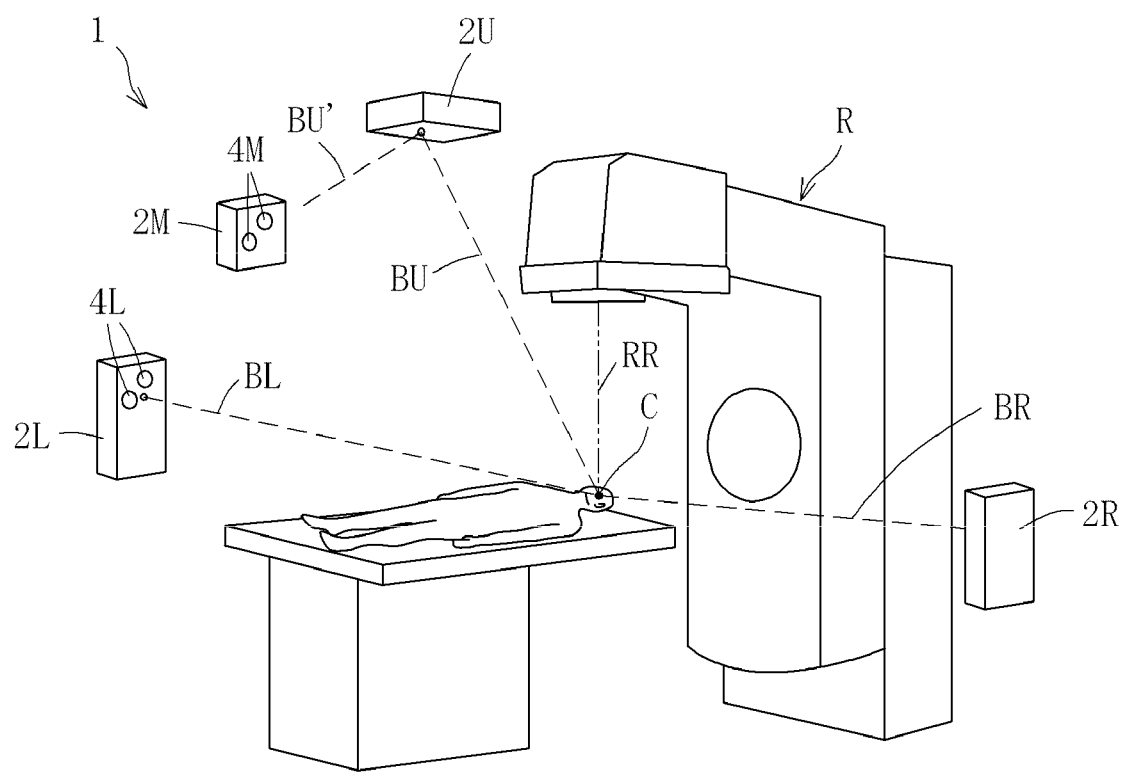
FIG. 1 is a perspective view illustrating a radiation therapy apparatus to which is applied an optical beam pointing system according to the present invention.
Figure 2:
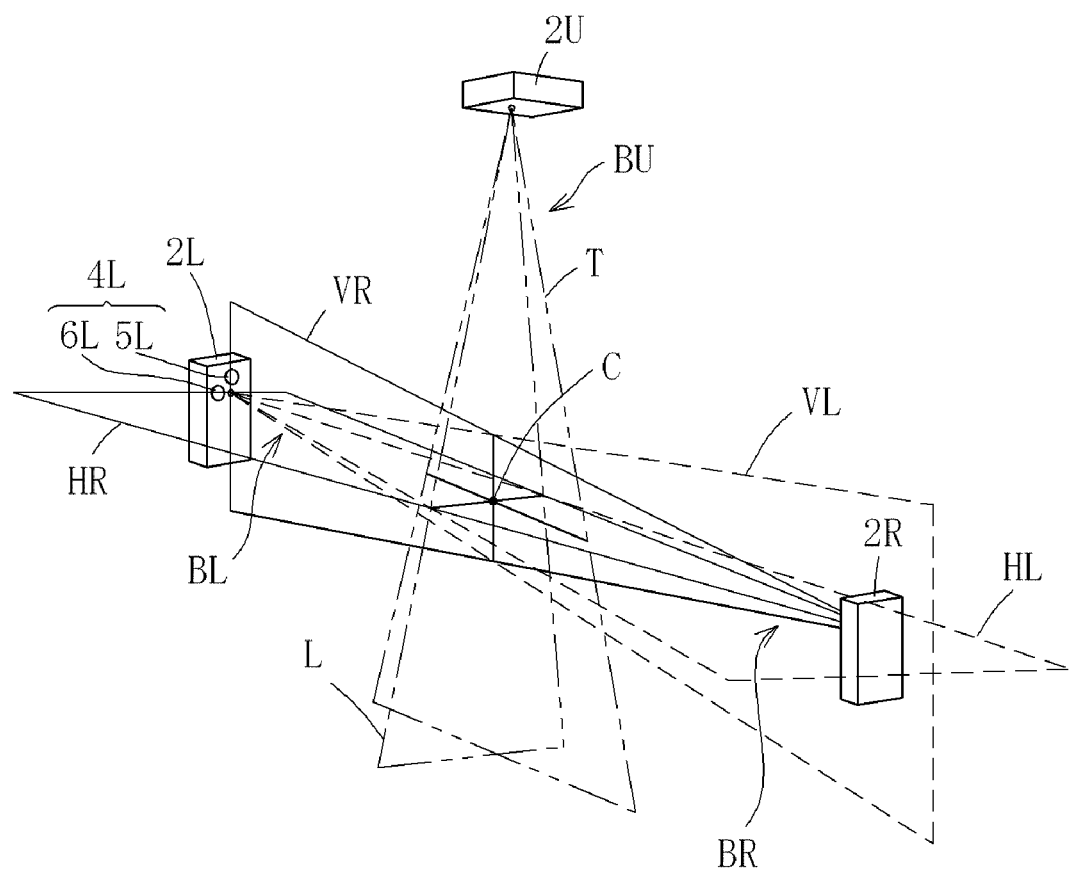
FIG. 2 is a schematic perspective view illustrating visible light beams projected from the optical beam pointing system in FIG. 1.
Figure 3:
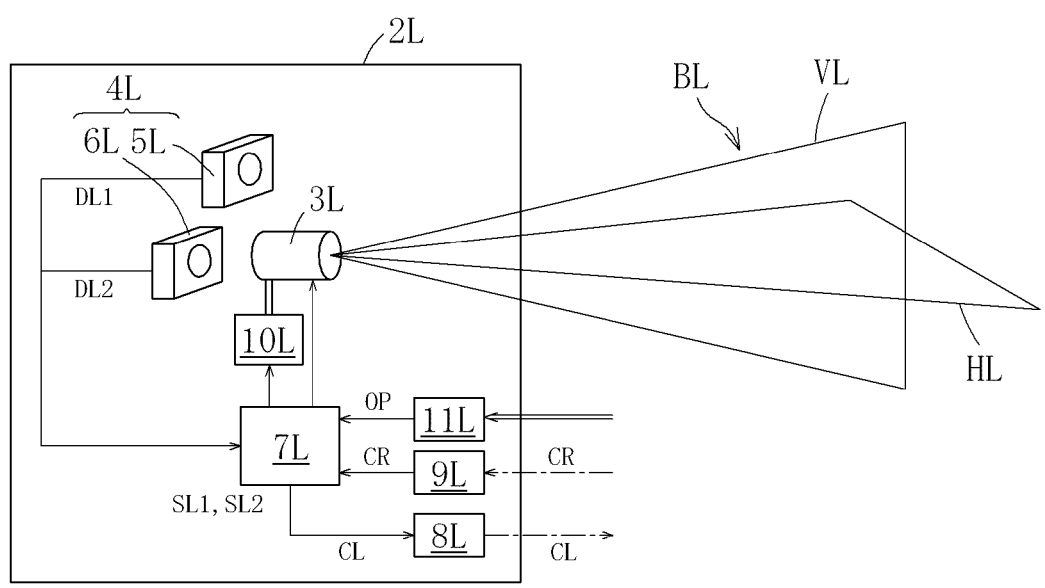
FIG. 3 is a schematic diagram illustrating optical beam pointers included in the optical beam pointing system in FIG. 1.
Figure 3:
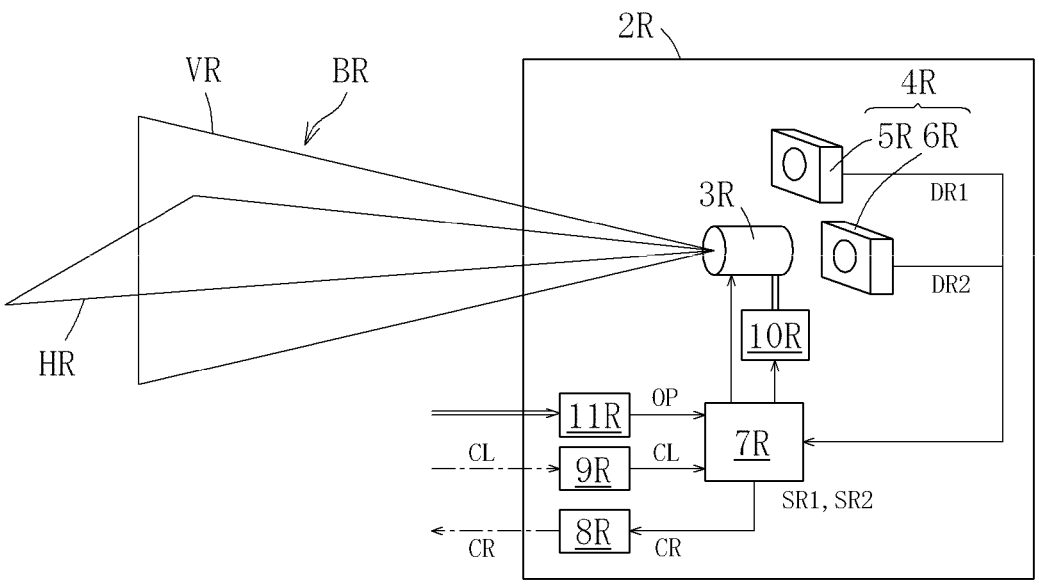
Figure 4:
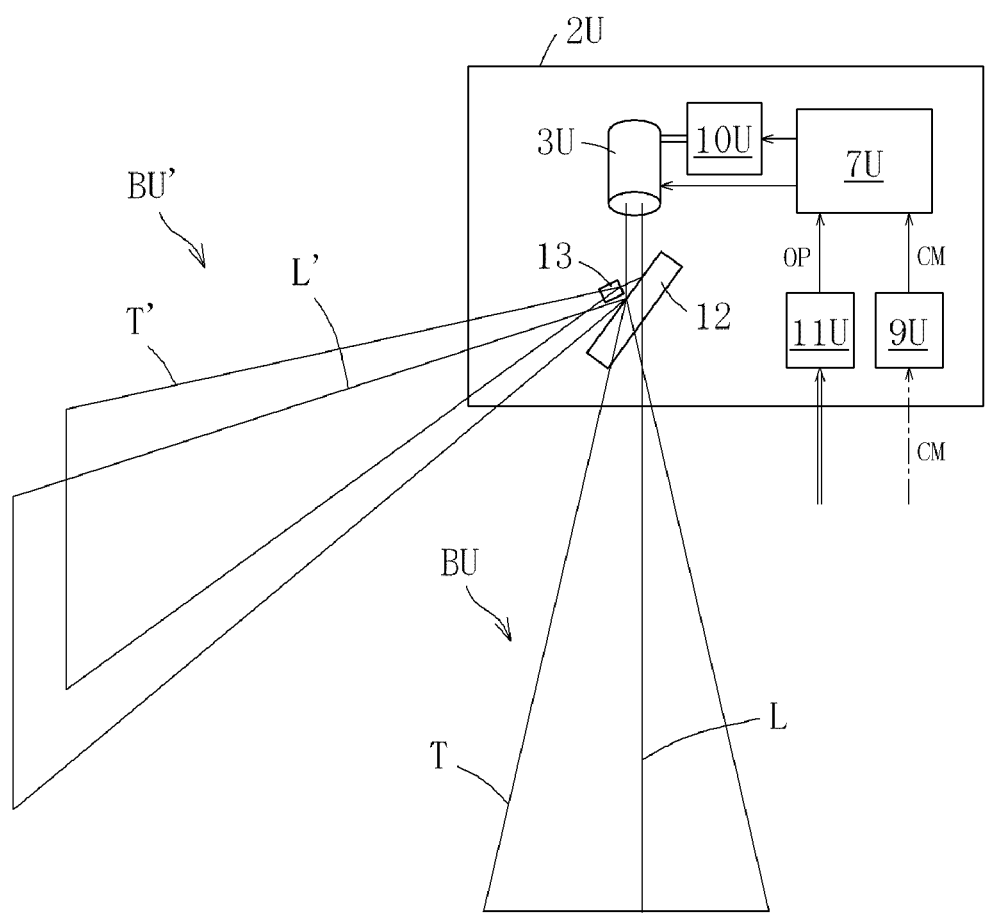
FIG. 4 is another schematic diagram illustrating optical beam pointers included in the optical beam pointing system in FIG. 1.
Figure 5:
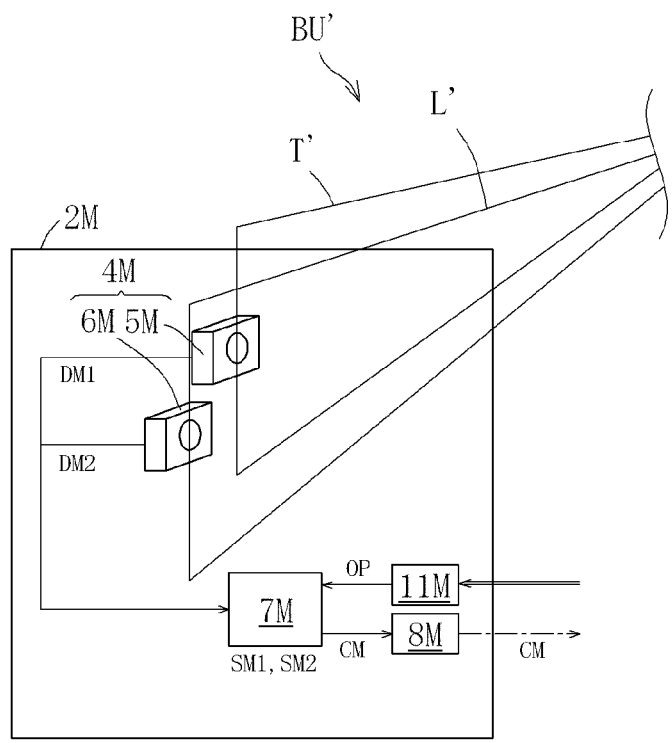
FIG. 5 is a schematic diagram illustrating an optical beam monitoring device included in the optical beam pointing system in FIG. 1.
Figure 6:
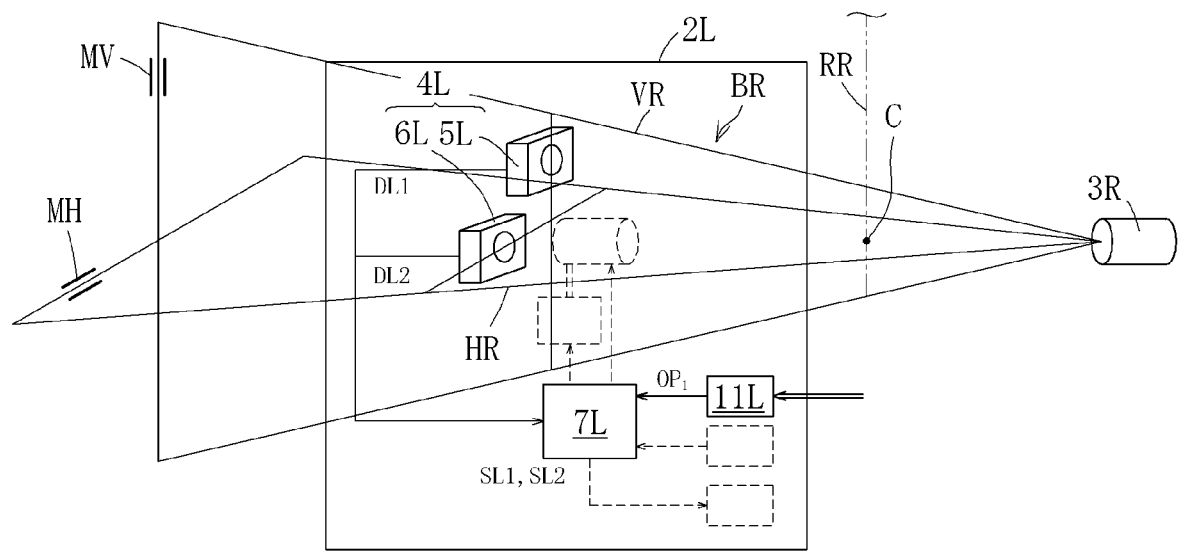
FIG. 6 is a schematic diagram for explaining the procedure for storing reference values in the optical beam pointing system in FIG. 1.
Figure 7:
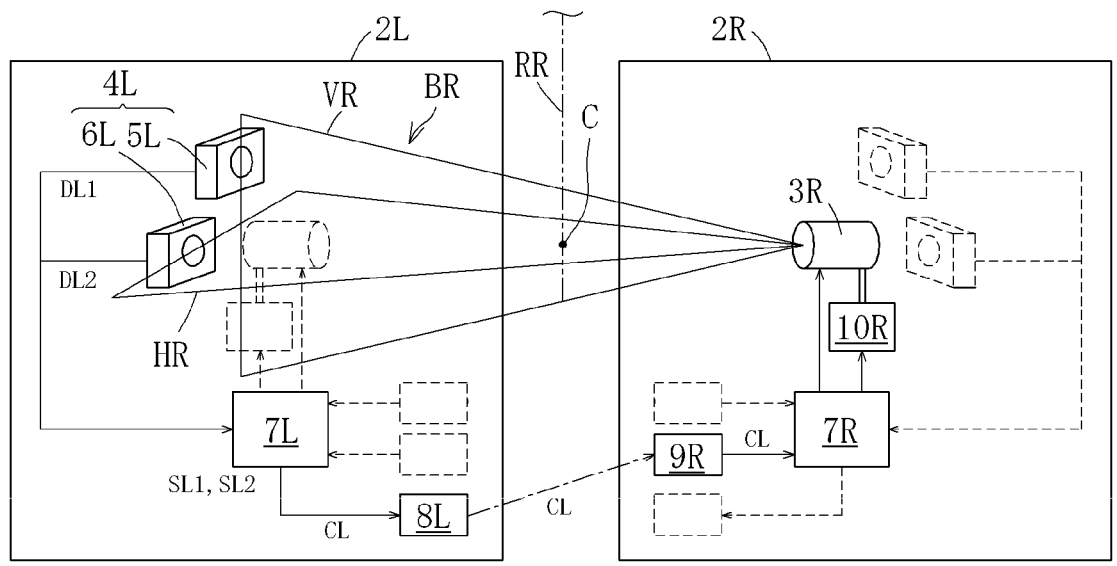
FIG. 7 is a schematic diagram for explaining the operation of the optical beam pointing system in FIG. 1.
Figure 7:
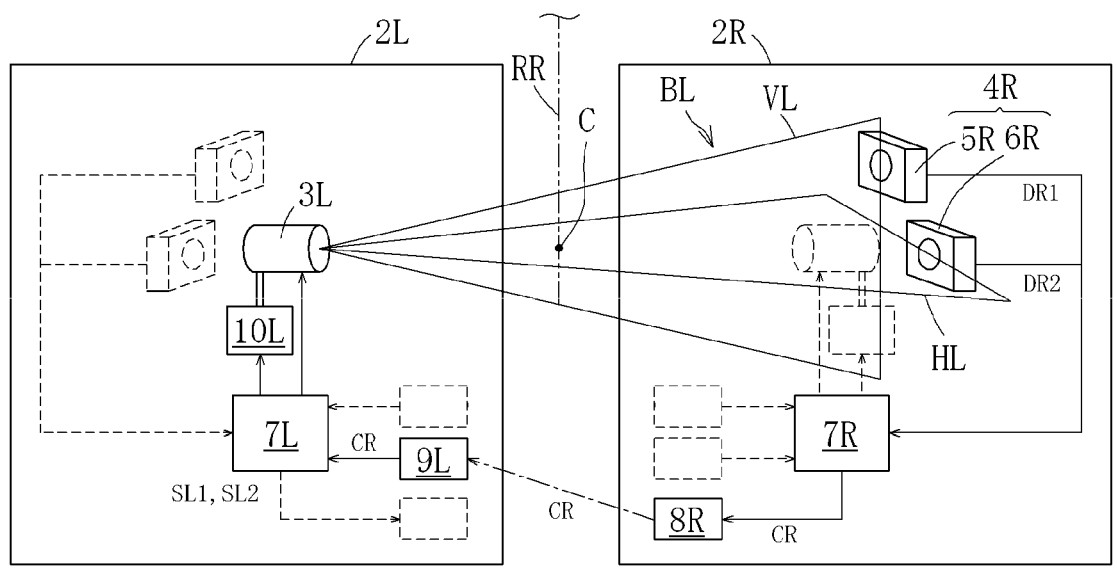
Figure 8:
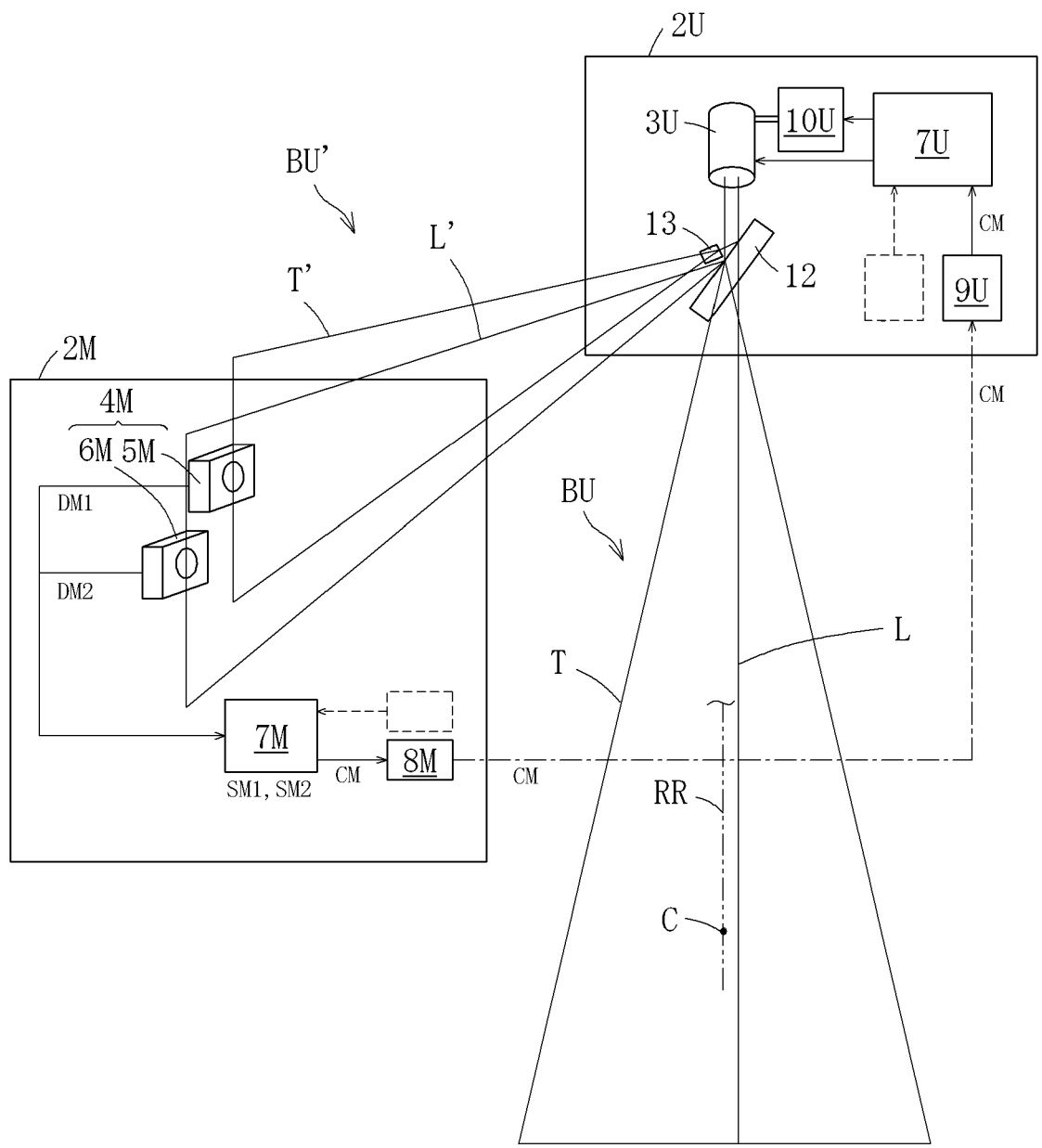
FIG. 8 is another schematic diagram for explaining the operation of the optical beam pointing system in FIG. 1.

FIG. 1 is a perspective view illustrating a radiation therapy apparatus to which is applied an optical beam pointing system according to the present invention, FIG. 2 is a schematic perspective view illustrating visible light beams projected from the optical beam pointing system in FIG. 1, FIGS. 3 and 4 are schematic diagrams illustrating optical beam pointers included in the optical beam pointing system in FIG. 1, FIG. 5 is a schematic diagram illustrating an optical beam monitoring device included in the optical beam pointing system in FIG. 1, FIG. 6 is a schematic diagram for explaining the procedure for storing reference values in the optical beam pointing system in FIG. 1, and FIGS. 7 and 8 are schematic diagrams for explaining the operation of the optical beam pointing system in FIG. 1.

As shown in FIG. 1, the optical beam pointing system 1 according to the present invention includes a left optical beam pointer (first optical beam pointer) 2L and a right optical beam pointer (second optical beam pointer) 2R, which are disposed laterally to an irradiation center C for radiation RR from the radiation therapy apparatus R, as well as an upper optical beam pointer (third optical beam pointer) 2U disposed above the irradiation center C, and an optical beam monitoring device 2M disposed laterally to the upper optical beam pointer 2U.

The optical beam pointers 2L, 2R, and 2U respectively project visible light beams BL, BR, and BU (first, second, and third visible light beams) aimed at the irradiation center C, as shown in FIGS. 1 and 2. The left optical beam pointer 2L and the right optical beam pointer 2R are disposed in opposition to each other, and receive the visible light beam BL or BR from their opposing pointer, as will be described later. The upper optical beam pointer 2U includes a beam splitter 12, which splits the projected visible light beam BU, as will be described later (see FIGS. 4 and 8). As a result, a fractional light beam BU' is generated, traveling toward the below-described light-receiving portion 4M of the optical beam monitoring device 2M.

Here, the radiation therapy apparatus R is a linac or suchlike. In addition, when the radiation therapy apparatus R is of an isocentric type, the irradiation center C can be an isocenter.

[Configuration of the Left Optical Beam Pointer]

First, the configuration of the left optical beam pointer 2L will be described.

The left optical beam pointer 2L includes a projecting portion 3L (a first projecting portion) for projecting the visible light beam BL, and a light-receiving portion 4L (a first light-receiving portion) for receiving the visible light beam BR from the right optical beam pointer 2R, as shown in A of FIG. 3.

The projecting portion 3L projects the visible light beam BL, such as a laser beam. The projecting portion 3L forms the visible light beam BL in the shape of a cross by projecting a vertical beam VL (a first vertical beam), which spreads vertically, and a horizontal beam HL (a first horizontal beam), which spreads horizontally.

The light-receiving portion 4L consists of optical receivers (first optical receivers) 5L and 6L, each being composed of, for example, a PSD optical receiver, a CCD optical receiver, or a CMOS optical receiver. The optical receiver 5L generates a detection signal (first detection signal) DL1 in accordance with the receiving position at which is received the below-described vertical beam VR (a second vertical beam) included in the visible light beam BR. Similarly, the optical receiver 6L generates a detection signal (first detection signal) DL2 in accordance with the receiving position at which is received the below-described horizontal beam HR (a second vertical beam) included in the visible light beam BR.

In addition, the left optical beam pointer 2L includes a control portion (first control portion) 7L for receiving the detection signals DL1 and DL2 from the optical receivers 5L and 6L, as shown in A of FIG. 3.

The control portion 7L has stored therein reference values (first reference values) SL1 and SL2 for the detection signals DL1 and DL2 from the optical receivers 5L and 6L. The reference values SL1 and SL2 are values for the detection signals DL1 and DL2 to be generated when the optical receivers 5L and 6L receive the vertical beam VR and the horizontal beam HR projected from the right optical beam pointer 2R and passing through the irradiation center C for the radiation therapy apparatus R as aimed. That is, the vertical beam VR and the horizontal beam HR having normally passed through the irradiation center C have been previously received by the optical receivers 5L and 6L, and the detection signals DL1 and DL2 at that time have been stored in the control portion 7L as the reference values SL1 and SL2, as will be described later.

In addition, the control portion 7L compares the detection signals DL1 and DL2 received from the optical receivers 5L and 6L with the previously stored reference values SL1 and SL2. When the comparison results show that the differences between the detection signals DL1 and DL2 and the reference values SL1 and SL2 fall outside a predetermined tolerable range, the control portion 7L generates a correction signal (first correction signal) CL for correcting the projection angle of the below-described projecting portion 3R (a second projecting portion) in the right optical beam pointer 2R.

In addition, the left optical beam pointer 2L includes a transmitting portion (first transmitting portion) 8L for transmitting the correction signal CL to the right optical beam pointer 2R upon reception of the signal CL from the control portion 7L, as shown in A of FIG. 3.

The transmitting portion 8L transmits the correction signal CL received from the control portion 7L to the below-described receiving portion (second receiving portion) 9R in the right optical beam pointer 2R. At this time, the transmitting portion 8L transmits the correction signal CL wirelessly, e.g., via infrared, to the receiving portion 9R.

In addition, as shown in A of FIG. 3, the left optical beam pointer 2L includes a receiving portion 9L (a first receiving portion) for receiving a correction signal (second correction signal) CR from the below-described transmitting portion (second transmitting portion) 8R in the right optical beam pointer 2R.

The receiving portion 9L is adapted to receive the correction signal CR wirelessly, e.g., via infrared, from the transmitting portion 8R of the right optical beam pointer 2R.

In addition, the left optical beam pointer 2L includes an actuator (first actuator) 10L for correcting the projection angle of the projecting portion 3L in accordance with the correction signal CR received by the receiving portion 9L, as shown in A of FIG. 3.

The actuator 10L is mechanically connected to the projecting portion 3L, and changes the inclination of the projecting portion 3L based on the correction signal CR received by the control portion 7L from the receiving portion 9L, thereby correcting the projection angle of the projecting portion 3L. Here, the actuator 10L can correct both the projection angles of the vertical beam VL and the horizontal beam HL constituting the visible light beam BL. Accordingly, after the correction, the projecting portion 3L projects the vertical beam VL and the horizontal beam HL so as to normally pass through the irradiation center C for the radiation therapy apparatus R.

In addition, the left optical beam pointer 2L includes an interface portion 11L for receiving user operations, as shown in A of FIG. 3.

The interface portion 11L generates various operation signals OP in response to various user operations. The control portion 7L controls various elements and changes their settings (e.g., the projecting portion 3L is caused to start projection) in accordance with the operation signals OP received from the interface portion 11L. For example, upon reception of a user operation for setting the reference values (a first setting operation), the interface portion 11L generates an operation signal OP1 associated with storing the reference values. The control portion 7L having received the operation signal OP1 stores, as the reference values SL1 and SL2, the detection signals DL1 and DL2 being received at that time from the optical receivers 5L and 6L.

[Configuration of the Right Optical Beam Pointer]

Next, the configuration of the right optical beam pointer 2R will be described.

The right optical beam pointer 2R includes a projecting portion 3R for projecting the visible light beam BR, and a light-receiving portion 4R (a second light-receiving portion) for receiving the visible light beam BL from the left optical beam pointer 2L, as shown in B of FIG. 3.

The projecting portion 3R projects the visible light beam BR, such as a laser beam. The projecting portion 3R forms the visible light beam BR in the shape of a cross by projecting the vertical beam VR, which spreads vertically, and the horizontal beam HR, which spreads horizontally.

The light-receiving portion 4R consists of optical receivers (second optical receivers) 5R and 6R, each being composed of, for example, a PSD optical receiver, a CCD optical receiver, or a CMOS optical receiver. The optical receiver 5R generates a detection signal (second detection signal) DR1 in accordance with the receiving position at which is received the vertical beam VL included in the visible light beam BL. Similarly, the optical receiver 6R generates a detection signal (second detection signal) DR2 in accordance with the receiving position at which is received the horizontal beam HL included in the visible light beam BL.

In addition, the right optical beam pointer 2R includes a control portion (second control portion) 7R for receiving the detection signals DR1 and DR2 from the optical receivers 5R and 6R, as shown in B of FIG. 3.

The control portion 7R has stored therein reference values (second reference values) SR1 and SR2 for the detection signals DR1 and DR2 from the optical receivers 5R and 6R. The reference values SR1 and SR2 are values for the detection signals DR1 and DR2 to be generated when the optical receivers 5R and 6R receive the vertical beam VL and the horizontal beam HL projected from the left optical beam pointer 2L and passing through the irradiation center C for the radiation therapy apparatus R as aimed. That is, the vertical beam VL and the horizontal beam HL having normally passed through the irradiation center C have been previously received by the optical receivers 5R and 6R, and the detection signals DR1 and DR2 at that time have been stored in the control portion 7R as the reference values SR1 and SR2.

In addition, the control portion 7R compares the detection signals DR1 and DR2 received from the optical receivers 5R and 6R with the previously stored reference values SR1 and SR2. When the comparison results show that the differences between the detection signals DR1 and DR2 and the reference values SR1 and SR2 fall outside a predetermined tolerable range, the control portion 7R generates a correction signal CR for correcting the projection angle of the projecting portion 3L in the left optical beam pointer 2L.

In addition, the right optical beam pointer 2R includes a transmitting portion 8R for transmitting the correction signal CR to the left optical beam pointer 2L upon reception of the signal CR from the control portion 7R, as shown in B of FIG. 3.

The transmitting portion 8R transmits the correction signal CR received from the control portion 7R to the receiving portion 9L in the left optical beam pointer 2L. At this time, the transmitting portion 8R transmits the correction signal CR wirelessly, e.g., via infrared, to the receiving portion 9L.

In addition, the right optical beam pointer 2R includes a receiving portion 9R for receiving the correction signal CL from the transmitting portion 8L in the left optical beam pointer 2L, as shown in B of FIG. 3.

The receiving portion 9R is adapted to receive the correction signal CL wirelessly, e.g., via infrared, from the transmitting portion 8L of the left optical beam pointer 2L.

In addition, the right optical beam pointer 2R includes an actuator (second actuator) 10R for correcting the projection angle of the projecting portion 3R in accordance with the correction signal CL received by the receiving portion 9R, as shown in B of FIG. 3.

The actuator 10R is mechanically connected to the projecting portion 3R, and changes the inclination of the projecting portion 3R based on the correction signal CL received by the control portion 7R from the receiving portion 9R, thereby correcting the projection angle of the projecting portion 3R. Here, the actuator 10R can correct both the projection angles of the vertical beam VR and the horizontal beam HR constituting the visible light beam BR. Accordingly, after the correction, the projecting portion 3R projects the vertical beam VR and the horizontal beam HR so as to normally pass through the irradiation center C for the radiation therapy apparatus R.

In addition, the right optical beam pointer 2R includes an interface portion 11R for receiving user operations, as shown in B of FIG. 3.

The interface portion 11R generates various operation signals OP in response to various user operations. The control portion 7R controls various elements and changes their settings (e.g., the projecting portion 3R is caused to start projection) in accordance with the operation signals OP received from the interface portion 11R. For example, upon reception of a user operation for setting the reference values (a second setting operation), the interface portion 11R generates an operation signal OP2 associated with storing the reference values. The control portion 7R having received the operation signal OP2 stores, as the reference values SR1 and SR2, the detection signals DR1 and DR2 being received at that time from the optical receivers 5R and 6R.

[Configuration of the Upper Optical Beam Pointer]

Next, the configuration of the upper optical beam pointer 2U will be described.

The upper optical beam pointer 2U includes a projecting portion 3U (a third projecting portion) for projecting the visible light beam BU, and the beam splitter 12 for splitting the visible light beam BU, as shown in FIG. 4. The beam splitter 12 generates a fractional light beam BU' from the visible light beam BU, traveling toward the optical beam monitoring device 2M.

The projecting portion 3U projects the visible light beam BU, such as a laser beam, so as to extend vertically. The projecting portion 3U projects a traversal beam T, which spreads toward the left optical beam pointer 2L and the right optical beam pointer 2R, and a longitudinal beam L, which spreads perpendicular to the traversal beam T, thereby forming the visible light beam BU in the shape of a cross.

In addition, the upper optical beam pointer 2U includes a 90-degree rotating prism (optical element) 13 for rotating the spread directions of the longitudinal beam L included in the fractional light beam BU' by 90°, as shown in FIG. 4.

The 90-degree rotating prism 13 converts the longitudinal beam L included in the fractional light beam BU' into a vertical beam (fourth vertical beam) L' spreading vertically. Note that before passing through the 90-degree rotating prism 13, the longitudinal beam L included in the fractional light beam BU' is a horizontal beam (third horizontal beam) spreading horizontally. In addition, the traversal beam T included in the fractional light beam BU' does not pass through the 90-degree rotating prism 13. Therefore, the traversal beam T included in the fractional light beam BU' becomes a vertical beam (third vertical beam) T' spreading vertically without being rotated.

Note that the purpose of disposing the 90-degree rotating prism 13 is as follows.

Figure 9:
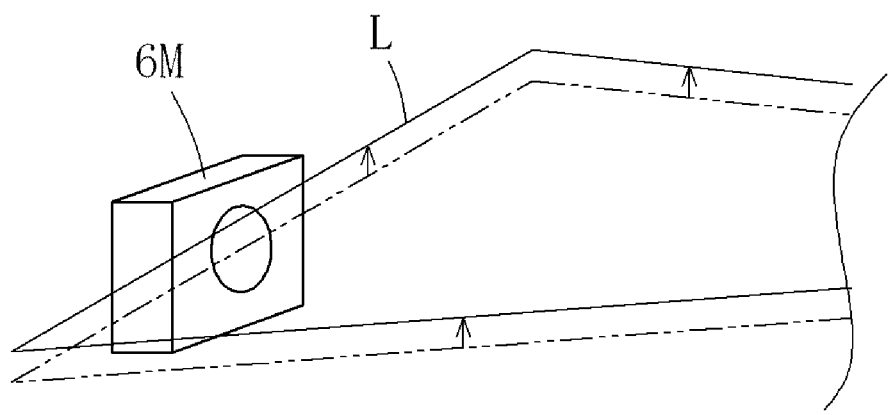
FIG. 9 is a schematic diagram for explaining the action of a 90-degree rotating prism.
Figure 9:
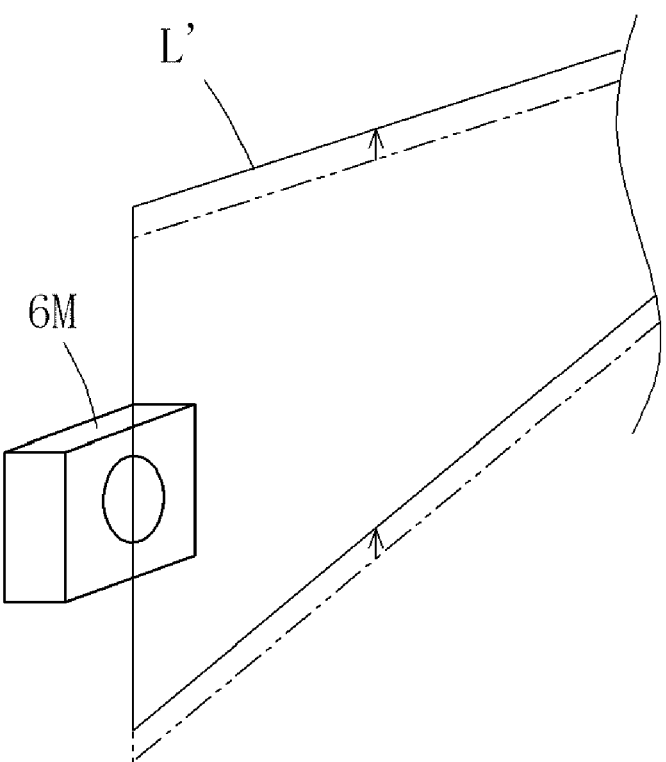

If the spread directions are not rotated by 90°, the longitudinal beam L is received as a horizontal beam by the below-described optical receiver 6M of the optical beam monitoring device 2M. In such a case, if the position of the entire upper optical beam pointer 2U is displaced vertically for some reason, the receiving position in the optical receiver 6M at which the longitudinal beam L is received changes vertically (see A of FIG. 9). In the case where the receiving position in the optical receiver 6M changes, the projection angle of the projecting portion 3U in the upper optical beam pointer 2U is corrected, as will be described later. However, the visible light beam 2U spreads vertically, and therefore, even if the position of the entire upper optical beam pointer 2U is displaced vertically, the position of the visible light beam BU at the irradiation center C is not displaced. As a result, correction is attempted by error, even though the projection angle requires no correction.

On the other hand, by disposing the 90-degree rotating prism 13, it becomes possible for the longitudinal beam L to be received by the optical receiver 6M as the vertical beam L'. In such a case, even if the position of the entire upper optical beam pointer 2U is displaced vertically, the receiving position in the optical receiver 6M does not change because the beam to be received is the vertical beam L' (see B of FIG. 9). Thus, it is possible to avoid the attempted correction of the projection angle by error.

In addition, the upper optical beam pointer 2U includes a receiving portion (third receiving portion) 9U for receiving a correction signal CM (a third correction signal) from the below-described transmitting portion (third transmitting portion) 8M in the optical beam monitoring device 2M, and a control unit 7U for receiving the correction signal CM from the receiving portion 9U, as shown in FIG. 4.

The receiving portion 9U is adapted to receive the correction signal CM wirelessly, e.g., via infrared, from the transmitting portion 8M in the optical beam monitoring device 2M.

In addition, the upper optical beam pointer 2U includes an actuator (third actuator) 10U for correcting the projection angle of the projecting portion 3U in accordance with the correction signal CM received by the receiving portion 9U, as shown in FIG. 4.

The actuator 10U is mechanically connected to the projecting portion 3U, and changes the inclination of the projecting portion 3U based on the correction signal CM received by the control unit 7U from the receiving portion 9U, thereby correcting the projection angle of the projecting portion 3U. Here, the actuator 10U can correct both the projection angles of the longitudinal beam L and the traversal beam T constituting the visible light beam BU. Accordingly, after the correction, the projecting portion 3U projects the longitudinal beam L and the traversal beam T so as to normally pass through the irradiation center C for the radiation therapy apparatus R.

In addition, the upper optical beam pointer 2U includes an interface portion 11U for receiving user operations, as shown in FIG. 4.

The interface portion 11U generates operation signals OP based on user operations. The control unit 7U controls various elements and changes their settings (e.g., the projecting portion 3U is caused to start projection) in accordance with the operation signals OP received from the interface portion 11U.

[Configuration of the Optical Beam Monitoring Device]

Next, the configuration of the optical beam monitoring device 2M will be described.

The optical beam monitoring device 2M includes a light-receiving portion 4M (a third light-receiving portion) for receiving the fractional light beam BU' from the upper optical beam pointer 2U, as shown in FIG. 5.

The light-receiving portion 4M consists of optical receivers (third optical receivers) 5M and 6M, each being composed of, for example, a PSD optical receiver, a CCD optical receiver, or a CMOS optical receiver. The optical receiver 5M generates a detection signal (third detection signal) DM1 in accordance with the receiving position at which is received the vertical beam T' included in the fractional light beam BU'. Similarly, the optical receiver 6M generates a detection signal (third detection signal) DM2 in accordance with the receiving position at which is received the vertical beam L' included in the fractional light beam BU'.

In addition, the optical beam monitoring device 2M includes a control portion (third control portion) 7M for receiving the detection signals DM1 and DM2 from the optical receivers 5M and 6M, as shown in FIG. 5.

The control portion 7M has stored therein reference values (third reference values) SM1 and SM2 for the detection signals DM1 and DM2 from the optical receivers 5M and 6M. The reference values SM1 and SM2 are values for the detection signal DM1 and DM2 to be generated when the optical receivers 5M and 6M receive the vertical beams T' and L' in the fractional light beam BU' split from the visible light beam BU derived from the upper optical beam pointer 2U and passing through the irradiation center C for the radiation therapy apparatus R as aimed. That is, the vertical beams T' and L' included in the fractional light beam BU' split from the visible light beam BU normally passing through the irradiation center C have been previously received by the optical receivers 5M and 6M, and the detection signals DM1 and DM2 at that time have been stored in the control portion 7M as the reference values SM1 and SM2.

In addition, the control portion 7M compares the detection signals DM1 and DM2 received from the optical receivers 5M and 6M with the previously stored reference values SM1 and SM2. If the comparison results show that the differences between the detection signals DM1 and DM2 and the reference values SM1 and SM2 fall outside a predetermined tolerable range, the control portion 7M generates the correction signal CM for correcting the projection angle of the projecting portion 3U in the upper optical beam pointer 2U.

In addition, the optical beam monitoring device 2M includes a transmitting portion (third transmitting portion) 8M for transmitting the correction signal CM to the upper optical beam pointer 2U upon reception of the signal CM from the control portion 7M, as shown in FIG. 5.

The transmitting portion 8M transmits the correction signal CM received from the control portion 7M to the receiving portion 9U in the upper optical beam pointer 2U. At this time, the transmitting portion 8M transmits the correction signal CM wirelessly, e.g., via infrared, to the receiving portion 9U.

In addition, the optical beam monitoring device 2M includes an interface portion 11M for receiving user operations, as shown in FIG. 5.

The interface portion 11M generates various operation signals OP in response to various user operations. The control portion 7M controls various elements and changes their settings in accordance with the operation signals OP received from the interface portion 11M. For example, upon reception of a user operation for setting the reference values (a third setting operation), the interface portion 11M generates an operation signal OP3 associated with storing the reference values. The control portion 7M having received the operation signal OP3 stores, as the reference values SM1 and SM2, the detection signals DM1 and DM2 being received at that time from the optical receivers 5M and 6M.

[Procedure for Storing the Reference Values]

Next, the procedure for storing the reference values SL1 and SL2 in the optical beam pointing system 1 will be described with reference to FIG. 6. Note that the procedures for storing reference values SR1, SR2, SM1, and SM2 are similar to that for the reference values SL1 and SL2, and therefore any descriptions thereof will be omitted. In addition, the storing operation needs to be performed only once when installing the optical beam pointing system 1 in the radiation therapy room, and no further storing operation is required thereafter.

(Step Z1)

First, the projection angle of the projecting portion 3R is adjusted such that the vertical beam VR and the horizontal beam HR from the projecting portion 3R in the right optical beam pointer 2R overlap with their respective marking-off lines MV and MH provided on the wall where the left optical beam pointer 2L is installed. Here, the marking-off lines MV and MH are provided on the wall at positions on which are incident the vertical beam VR and the horizontal beam HR, which have been previously adjusted so as to pass through the irradiation center C. Therefore, after the adjustment of the projection angle, the optical beam BR normally passes through the irradiation center C.

(Step Z2)

Next, the operator operates the interface portion 11L of the left optical beam pointer 2L to transmit the operation signal OP1 associated with storing the reference values to the control portion 7L.

(Step Z3)

The control portion 7L having received the operation signal OP1 stores, as the reference values SL1 and SL2, the detection signals DL1 and DL2 being received at that time from the optical receivers 5L and 6L. Thus, the operation of storing the reference values SL1 and SL2 is completed.

[Operation of the Optical Beam Pointing System]

Next, the operation of the optical beam pointing system 1 will be described with reference to FIGS. 7 and 8.

First, the description is focused on the visible light beam BR from the right optical beam pointer 2R.

(Step A1)

The right optical beam pointer 2R projects the visible light beam BR from the user projecting portion 3R, aimed at the irradiation center C for the radiation RR, as shown in A of FIG. 7.

(Step A2)

The visible light beam BR is received by the light-receiving portion 4L in the left optical beam pointer 2L. At this time, the vertical beam VR included in the visible light beam BR is received by the optical receiver 5L in the light-receiving portion 4L. Similarly, the horizontal beam HR included in the visible light beam BR is received by the optical receiver 6L in the light-receiving portion 4L.

(Step A3)

The optical receiver 5L having received the vertical beam VR generates the detection signal DL1 in accordance with the receiving position. Similarly, the optical receiver 6L having received the horizontal beam HR generates the detection signal DL2 in accordance with the receiving position.

(Step A4)

The generated detection signals DL1 and DL2 are received by the control portion 7L in the left optical beam pointer 2L. The control portion 7L having received the detection signals DL1 and DL2 compares the previously stored reference value SL1 with the received detection signal DL1. Similarly, the control portion 7L compares the previously stored reference value SL2 with the received detection signal DL2.

(Step A5)

When the comparison results show that the differences between the detection signals DL1 and DL2 and the reference values SL1 and SL2 fall above a predetermined tolerable range, it is the case where the visible light beam BR from the right optical beam pointer 2R has not normally passed through the irradiation center C. In such a case, the control portion 7L generates the correction signal CL to correct the projection angle of the projecting portion 3R in the right optical beam pointer 2R.

(Step A6)

The generated correction signal CL is received by the transmitting portion 8L in the left optical beam pointer 2L. The transmitting portion 8L having received the correction signal CL transmits the correction signal CL wirelessly to the receiving portion 9R in the right optical beam pointer 2R.

(Step A7)

The correction signal CL received by the receiving portion 9R is then received by the control portion 7R in the right optical beam pointer 2R. The control portion 7R having received the correction signal CL drives the actuator 10R in the right optical beam pointer 2R.

(Step A8)

The actuator 10R driven by the control portion 7R changes the inclination of the projecting portion 3R in the right optical beam pointer 2R based on the correction signal CL, thereby correcting the projection angle of the visible light beam BR. Note that the projection angles of the vertical beam VR and the horizontal beam HR constituting the visible light beam BR are corrected independently of each other.

With the correction, the visible light beam BR (the vertical beam VR and the horizontal beam HR) can normally pass through the irradiation center C.

When projecting the visible light beam BR, steps A1 to A4 as described above are always executed. If the projection angle of the visible light beam BR deviates again due to some factor, so that the light-receiving portion 4L in the left optical beam pointer 2L receives the visible light beam BR not passing through the irradiation center C, steps A5 to A8 as described above are executed to correct the projection angle of the visible light beam BR again.

Note that for the visible light beam BL from the left optical beam pointer 2L, the projection angle is corrected as in the above-described case of the visible light beam BR from the right optical beam pointer 2R (see B of FIG. 7), and therefore any detailed description thereof will be omitted.

Next, the description is focused on the visible light beam BU from the upper optical beam pointer 2U.

(Step B1)

The upper optical beam pointer 2U projects the visible light beam BU from the user projecting portion 3U, aimed at the irradiation center C for the radiation RR, as shown in FIG. 8. The visible light beam BU is split by the beam splitter 12, thereby generating the fractional light beam BU' traveling toward the optical beam monitoring device 2M.

Note that, as described above, by passing through the 90-degree rotating prism 13, the longitudinal beam L included in the fractional light beam BU' is converted into the vertical beam L' spreading vertically. On the other hand, the traversal beam T included in the fractional light beam BU' becomes the vertical beam T' spreading vertically without being rotated.

(Step B2)

The fractional light beam BU' is received by the light-receiving portion 4M in the optical beam monitoring device 2M. At this time, the vertical beam T' included in the fractional light beam BU' is received by the optical receiver 5M in the light-receiving portion 4M. Similarly, the vertical beam L' included in the fractional light beam BU' is received by the optical receiver 6M in the light-receiving portion 4M.

(Step B3)

The optical receiver 5M having received the vertical beam T' generates the detection signal DM1 in accordance with the receiving position. Similarly, the optical receiver 6M having received the vertical beam L' generates the detection signal DM2 in accordance with the receiving position.

(Step B4)

The generated detection signals DM1 and DM2 are received by the control portion 7M in the optical beam monitoring device 2M. The control portion 7M having received the detection signals DM1 and DM2 compares the previously stored reference value SM1 with the received detection signal DM1. Similarly, the control portion 7M compares the previously stored reference value SM2 with the received detection signal DM2.

(Step B5)

When the comparison results show that the differences between the detection signals DM1 and DM2 and the reference values SM1 and SM2 fall above a predetermined tolerable range, it is the case where the visible light beam BU from the upper optical beam pointer 2U has not normally passed through the irradiation center C. In such a case, the control portion 7M generates the correction signal CM to correct the projection angle of the projecting portion 3U in the upper optical beam pointer 2U.

(Step B6)

The generated correction signal CM is received by the transmitting portion 8M in the optical beam monitoring device 2M. The transmitting portion 8M having received the correction signal CM transmits the correction signal CM wirelessly to the receiving portion 9U in the upper optical beam pointer 2U.

(Step B7)

The correction signal CM received by the receiving portion 9U is then received by the control portion 7U in the upper optical beam pointer 2U. The control portion 7U having received the correction signal CM drives the actuator 10U in the upper optical beam pointer 2U.

(Step B8)

The actuator 10U driven by the control portion 7U changes the inclination of the projecting portion 3U in the upper optical beam pointer 2U based on the correction signal CM, thereby correcting the projection angle of the visible light beam BU. Note that the projection angles of the longitudinal beam L and the traversal beam T constituting the visible light beam BU are corrected independently of each other. In addition, by correcting the projection angle of the visible light beam BU, the projection angle of the fractional light beam BU' is corrected as well.

With the correction, the visible light beam BU (the longitudinal beam L and the traversal beam T) can normally pass through the irradiation center C.

When projecting the visible light beam BU, steps B1 to B4 as described above are always executed. If the projection angle of the visible light beam BU deviates again due to some factor, so that the light-receiving portion 4M in the optical beam monitoring device 2M receives the fractional light beam BU' split from the visible light beam BU not passing through the irradiation center C, steps B5 to B8 as described above are executed to correct the projection angle of the visible light beam BU again.

[Effects of the Optical Beam Pointing System]

According to the optical beam pointing system 1 configured as described above, the projection angles of the visible light beams BL, BR, and BU are always automatically corrected while the visible light beams BL, BR, and BU are being projected, so that the irradiation center C for the radiation RR from the radiation therapy apparatus R can always be accurately pointed. Therefore, maintenance workers do not have to adjust the projection angles of the visible light beams BL, BR, and BU each time such an adjustment is required. In addition, there is no possibility of causing variations in projection angle adjustment among maintenance workers.

Also, in the optical beam pointing system 1, the beam splitter 12 generates the fractional light beam BU' traveling laterally based on the visible light beam BU from the upper optical beam pointer 2U, and the projection angle of the visible light beam BU is corrected based on the receiving position of the fractional light beam BU'. Therefore, the optical beam monitoring device 2M for correcting the projection angle of the visible light beam BU is not required to be disposed on the line along which the visible light beam BU travels, i.e., in an area where the radiation RR travels or in an area occupied by the patient.

Also, the upper optical beam pointer 2U includes the 90-degree rotating prism 13 for converting the longitudinal beam L included in the fractional light beam BU' into the vertical beam L' by rotating the spread directions thereof by 90°. Therefore, for example, when the position of the entire upper optical beam pointer 2U is displaced only vertically, i.e., when the upper optical beam pointer 2U does not deviate with respect to the irradiation center C for the visible light beam BU, the receiving position in the optical receiver 6M at which the vertical beam L' is received in the optical beam monitoring device 2M does not change. Thus, it is possible to avoid the situation where the projection angle is attempted to be corrected by error even though it should not be corrected.

Also, in the optical beam pointing system 1, the correction signals CL, CR, and CM are wirelessly received/transmitted. Therefore, no wiring is required between the left optical beam pointer 2L and the right optical beam pointer 2R and between the upper optical beam pointer 2U and the optical beam monitoring device 2M, which facilitates installation into the radiation therapy room.

[Variations]

While the foregoing description has been given in detail with respect to an embodiment of the present invention, the present invention can be carried out with the following variations.

For example, in the above embodiment, the determination as to whether the visible light beam misses the irradiation center is made by the optical beam pointer having received the visible light beam targeted for determination or by the optical beam monitoring device, but such a determination may be made by the optical beam pointer having projected the visible light beam targeted for determination. In such a case, the receiving-side optical beam pointer or the optical beam monitoring device always transmits a detection signal to the projecting-side optical beam pointer. The projecting-side optical beam pointer having received the detection signal compares the detection signal with a reference value, which is similar to that in the above embodiment and stored in the control portion of the projecting-side optical beam pointer, thereby determining whether the visible light beam misses the irradiation center. If the determination result turns out to be a miss, the projecting-side optical beam pointer generates a correction signal to drive the actuator in the projecting-side optical beam pointer, thereby correcting the projection angle of the visible light beam.

The procedure for storing the reference value in such a configuration is as follows.

First, similar to step Z1 as described above, the projection angle of the projecting portion having projected the visible light beam targeted for determination is adjusted so as to overlap with the marking-off line provided on the wall on which the receiving-side optical beam pointer or the optical beam monitoring device is installed, i.e., the visible light beam targeted for determination normally passes through the irradiation center.

Next, the operator operates the interface portion in the receiving-side optical beam pointer or in the optical beam monitoring device (the first, second, or third setting operation) to transmit an operation signal associated with storing the reference value to the control portion in the receiving-side optical beam pointer or in the optical beam monitoring device.

The control portion having received the operation signal transmits an instruction signal (a first, second, or third instruction signal) to the receiving portion in the projecting-side optical beam pointer via the transmitting portion.

The projecting-side receiving portion having received the instruction signal transmits the received instruction signal to the projecting-side control portion. The projecting-side control portion having received the instruction signal stores, as a reference value, the detection signal being received (or having already been received) at that time by the projecting-side receiving portion. Thus, the operation of storing the reference value is completed.

Also, it is possible to omit the upper optical beam pointer and the optical beam monitoring device, so that the optical beam pointing system may be configured simply by the left optical beam pointer and the right optical beam pointer.

Also, the shape of the visible light beam is not limited to a cross, and may be linear, for example.

What is claimed is:

1. An optical beam pointing system for setting an irradiation position for radiation, the system pointing an irradiation center for radiation when positioning an irradiation target at the irradiation center, comprising:
    first and second optical beam pointers disposed on opposite sides of the irradiation center and opposed each other, wherein,
    the first optical beam pointer includes a first light-projecting portion for projecting a first visible light beam aimed at the irradiation center,
    the second optical beam pointer includes a second light-projecting portion for projecting a second visible light beam aimed at the irradiation center,
    the first optical beam pointer includes a first light-receiving portion for receiving the second visible light beam and generating a first detection signal in accordance with a receiving position at which the second visible light beam is received,
    the second optical beam pointer includes a second light-receiving portion for receiving the first visible light beam and generating a second detection signal in accordance with a receiving position at which the first visible light beam is received,
    the first optical beam pointer includes a first control portion having previously stored therein, as a first reference value, a value for the first detection signal to be generated by the first light-receiving portion which has received the second visible light beam passing through the irradiation center as aimed, the first control portion generating a first correction signal for correcting a projection angle of the second light-projecting portion when a difference between the first reference value and a value for the first detection signal actually generated by the first light-receiving portion falls outside a tolerable range,
    the second optical beam pointer includes a second control portion having previously stored therein, as a second reference value, a value for the second detection signal to be generated by the second light-receiving portion which has received the first visible light beam passing through the irradiation center as aimed, the second control portion generating a second correction signal for correcting a projection angle of the first light-projecting portion when a difference between the second reference value and a value for the second detection signal actually generated by the second light-receiving portion falls outside a tolerable range,
    the first optical beam pointer includes a first transmitting portion for transmitting the first correction signal to the second optical beam pointer,
    the second optical beam pointer includes a second transmitting portion for transmitting the second correction signal to the first optical beam pointer,
    the first optical beam pointer includes a first receiving portion for receiving the second correction signal from the second transmitting portion,
    the second optical beam pointer includes a second receiving portion for receiving the first correction signal from the first transmitting portion,
    the first optical beam pointer includes a first actuator for correcting a projection angle of the first light-projecting portion in accordance with the second correction signal received by the first receiving portion, such that the first visible light beam passes through the irradiation center, and
    the second optical beam pointer includes a second actuator for correcting a projection angle of the second light-projecting portion in accordance with the first correction signal received by the second receiving portion, such that the second visible light beam passes through the irradiation center.

2. The optical beam pointing system according to claim 1, wherein,
    the first optical beam pointer further includes a first interface portion,
    the first control portion is adapted to store, as the first reference value, the first detection signal generated by the first light-receiving portion when the first interface portion receives a user's first setting operation, the second optical beam pointer further includes a second interface portion, and the second control portion is adapted to store, as the second reference value, the second detection signal generated by the second light-receiving portion when the second interface portion receives a user's second setting operation.

3. The optical beam pointing system according to claim 2, wherein, the first light-projecting portion is adapted to project the first visible light beam in the shape of a cross consisting of a first vertical beam spreading vertically and a first horizontal beam spreading horizontally, the second light-projecting portion is adapted to project the second visible light beam in the shape of a cross consisting of a second vertical beam spreading vertically and a second horizontal beam spreading horizontally, the first light-receiving portion consists of two first optical receivers, one for receiving the second vertical beam, the other for receiving the second horizontal beam, and the second light-receiving portion consists of two second optical receivers, one for receiving the first vertical beam, the other for receiving the first horizontal beam.

4. The optical beam pointing system according to claim 3, wherein each signal is wirelessly received/transmitted between the first transmitting portion and the second receiving portion and/or between the second transmitting portion and the first receiving portion.

5. The optical beam pointing system according to claim 4, further comprising:

a third optical beam pointer disposed above the irradiation center; and an optical beam monitoring device disposed laterally to the third optical beam pointer, wherein, the third optical beam pointer includes:
a third light-projecting portion for projecting a third visible light beam aimed at the irradiation center; and
a beam splitter for generating a fractional light beam from the third visible light beam, the fractional light beam traveling toward the optical beam monitoring device, the optical beam monitoring device includes:
a third light-receiving portion for receiving the fractional light beam and generating a third detection signal in accordance with a receiving position at which the fractional light beam is received;
a third control portion having previously stored therein, as a third reference value, a value for the third detection signal to be generated by the third light-receiving portion which has received the fractional light beam derived from the third visible light beam passing through the irradiation center as aimed, the third control portion generating a third correction signal for correcting a projection angle of the third light-projecting portion when a difference between the third reference value and a value for the third detection signal actually generated by the third light-receiving portion falls outside a tolerable range, and
a third transmitting portion for transmitting the third correction signal to the third optical beam pointer, and the third optical beam pointer includes:
a third receiving portion for receiving the third correction signal from the third transmitting portion; and
a third actuator for correcting a projection angle of the third light-projecting portion in accordance with the third correction signal received by the third receiving portion, such that the third visible light beam passes through the irradiation center.

6. The optical beam pointing system according to claim 5, wherein, the optical beam monitoring device further includes a third interface portion, and the third control portion is adapted to store, as the third reference value, the third detection signal generated by the third light-receiving portion when the third interface portion receives a user's third setting operation.

7. The optical beam pointing system according to claim 6, wherein, the third light-projecting portion is adapted to project the third visible light beam traveling vertically in the shape of a cross consisting of a traversal beam spreading along the line connecting the first optical beam pointer and the second optical beam pointer, and a longitudinal beam spreading perpendicular to the traversal beam, the longitudinal beam is converted by the beam splitter into a third horizontal beam spreading horizontally, the third horizontal beam forming a part of the fractional light beam, the traversal beam is converted by the beam splitter into a third vertical beam spreading vertically, the third vertical beam forming the other part of the fractional light beam, the third optical beam pointer further includes a optical element for converting the third horizontal beam into a fourth vertical beam spreading vertically by rotating spread directions of the third horizontal beam by 90°, and the third light-receiving portion consists of two third optical receivers, one for receiving the third vertical beam, the other for receiving the fourth vertical beam.

8. The optical beam pointing system according to claim 6, wherein each signal is wirelessly received/transmitted between the third transmitting portion and the third receiving portion.

9. The optical beam pointing system according to claim 4, further comprising:

a third optical beam pointer disposed above the irradiation center; and an optical beam monitoring device disposed laterally to the third optical beam pointer, wherein, the third optical beam pointer includes:
a third light-projecting portion for projecting a third visible light beam aimed at the irradiation center; and
a beam splitter for generating a fractional light beam from the third visible light beam, the fractional light beam traveling toward the optical beam monitoring device, the optical beam monitoring device includes:
a third light-receiving portion for receiving the fractional light beam and generating a third detection signal in accordance with a receiving position at which the fractional light beam is received; and
a third transmitting portion for transmitting the third detection signal to the third optical beam pointer, and the third optical beam pointer includes:
a third receiving portion for receiving the third detection signal from the third transmitting portion;
a third control portion having previously stored therein, as a third reference value, a value for the third detection signal to be generated by the third light-receiving portion which has received the fractional light beam derived from the third visible light beam passing through the irradiation center as aimed, the third control portion generating a third correction signal for correcting a projection angle of the third light-projecting portion when a difference between the third reference value and a value for the third detection signal received by the third receiving portion falls outside a tolerable range; and a third actuator for correcting a projection angle of the third light-projecting portion in accordance with the third correction signal, such that the third visible light beam passes through the irradiation center.

10. The optical beam pointing system according to claim 9, wherein,
the optical beam monitoring device further includes:
a third interface portion; and
a fourth control portion electrically connected to at least the third interface portion and the third transmitting portion,
the fourth control portion transmits a third instruction signal to the third receiving portion via the third transmitting portion when the third interface portion receives a user's third setting operation, and
the third control portion is adapted to store, as the third reference value, the third detection signal received by the third receiving portion when the third control portion receives the third instruction signal via the third receiving portion.

11. The optical beam pointing system according to claim 10, wherein,
the third light-projecting portion is adapted to project the third visible light beam traveling vertically in the shape of a cross consisting of a traversal beam spreading along the line connecting the first optical beam pointer and the second optical beam pointer, and a longitudinal beam spreading perpendicular to the traversal beam,
the longitudinal beam is converted by the beam splitter into a third horizontal beam spreading horizontally, the third horizontal beam forming a part of the fractional light beam,
the traversal beam is converted by the beam splitter into a third vertical beam spreading vertically, the third vertical beam forming the other part of the fractional light beam,
the third optical beam pointer further includes a optical element for converting the third horizontal beam into a fourth vertical beam spreading vertically by rotating spread directions of the third horizontal beam by 90°, and
the third light-receiving portion consists of two third optical receivers, one for receiving the third vertical beam, the other for receiving the fourth vertical beam.

12. The optical beam pointing system according to claim 10, wherein each signal is wirelessly received/transmitted between the third transmitting portion and the third receiving portion.

13. An optical beam pointing system for setting an irradiation position for radiation, the system pointing an irradiation center for radiation when positioning an irradiation target at the irradiation center, comprising:
first and second optical beam pointers disposed on opposite sides of the irradiation center and opposed each other, wherein,
the first optical beam pointer includes a first light-projecting portion for projecting a first visible light beam aimed at the irradiation center,
the second optical beam pointer includes a second light-projecting portion for projecting a second visible light beam aimed at the irradiation center, the first optical beam pointer includes a first light-receiving portion for receiving the second visible light beam and generating a first detection signal in accordance with a receiving position at which the second visible light beam is received,
the second optical beam pointer includes a second light-receiving portion for receiving the first visible light beam and generating a second detection signal in accordance with a receiving position at which the first visible light beam is received,
the first optical beam pointer includes a first transmitting portion for transmitting the first detection signal to the second optical beam pointer,
the second optical beam pointer includes a second transmitting portion for transmitting the second detection signal to the first optical beam pointer,
the first optical beam pointer includes a first receiving portion for receiving the second detection signal from the second transmitting portion,
the second optical beam pointer includes a second receiving portion for receiving the first detection signal from the first transmitting portion,
the first optical beam pointer includes a first control portion having previously stored therein, as a second reference value, a value for the second detection signal to be generated by the second light-receiving portion which has received the first visible light beam passing through the irradiation center as aimed, the first control portion generating a second correction signal for correcting a projection angle of the first light-projecting portion when a difference between the second reference value and a value for the second detection signal received by the first receiving portion falls outside a tolerable range,
the second optical beam pointer includes a second control portion having previously stored therein, as a first reference value, a value for the first detection signal to be generated by the first light-receiving portion which has received the second visible light beam passing through the irradiation center as aimed, the second control portion generating a first correction signal for correcting a projection angle of the second light-projecting portion when a difference between the first reference value and a value for the first detection signal received by the second receiving portion falls outside a tolerable range,
the first optical beam pointer includes a first actuator for correcting a projection angle of the first light-projecting portion in accordance with the second correction signal, such that the first visible light beam passes through the irradiation center, and
the second optical beam pointer includes a second actuator for correcting a projection angle of the second light-projecting portion in accordance with the first correction signal, such that the second visible light beam passes through the irradiation center.

14. The optical beam pointing system according to claim 13, wherein,
the first optical beam pointer further includes a first interface portion,
the first control portion transmits a first instruction signal to the second receiving portion via the first transmitting portion when the first interface portion receives a user's first setting operation,
the second control portion is adapted to store, as the first reference value, the first detection signal received by the second receiving portion when the second control portion receives the first instruction signal via the second receiving portion, the second optical beam pointer further includes a second interface portion, the second control portion transmits a second instruction signal to the first receiving portion via the second transmitting portion when the second interface portion receives a user's second setting operation, and the first control portion is adapted to store, as the second reference value, the second detection signal received by the first receiving portion when the first control portion receives the second instruction signal via the first receiving portion.

15. The optical beam pointing system according to claim 14, wherein, the first light-projecting portion is adapted to project the first visible light beam in the shape of a cross consisting of a first vertical beam spreading vertically and a first horizontal beam spreading horizontally, the second light-projecting portion is adapted to project the second visible light beam in the shape of a cross consisting of a second vertical beam spreading vertically and a second horizontal beam spreading horizontally, the first light-receiving portion consists of two first optical receivers, one for receiving the second vertical beam, the other for receiving the second horizontal beam, and the second light-receiving portion consists of two second optical receivers, one for receiving the first vertical beam, the other for receiving the first horizontal beam.

16. The optical beam pointing system according to claim 15, wherein each signal is wirelessly received/transmitted between the first transmitting portion and the second receiving portion and/or between the second transmitting portion and the first receiving portion.

17. The optical beam pointing system according to claim 16, further comprising:

a third optical beam pointer disposed above the irradiation center; and an optical beam monitoring device disposed laterally to the third optical beam pointer, wherein, the third optical beam pointer includes:
  a third light-projecting portion for projecting a third visible light beam aimed at the irradiation center; and
  a beam splitter for generating a fractional light beam from the third visible light beam, the fractional light beam traveling toward the optical beam monitoring device, the optical beam monitoring device includes:
  a third light-receiving portion for receiving the fractional light beam and generating a third detection signal in accordance with a receiving position at which the fractional light beam is received;
  a third control portion having previously stored therein, as a third reference value, a value for the third detection signal to be generated by the third light-receiving portion which has received the fractional light beam derived from the third visible light beam passing through the irradiation center as aimed, the third control portion generating a third correction signal for correcting a projection angle of the third light-projecting portion when a difference between the third reference value and a value for the third detection signal actually generated by the third light-receiving portion falls outside a tolerable range, and
  a third transmitting portion for transmitting the third correction signal to the third optical beam pointer, and the third optical beam pointer includes:
  a third receiving portion for receiving the third correction signal from the third transmitting portion; and
  a third actuator for correcting a projection angle of the third light-projecting portion in accordance with the third correction signal received by the third receiving portion, such that the third visible light beam passes through the irradiation center.

18. The optical beam pointing system according to claim 17, wherein, the optical beam monitoring device further includes a third interface portion, and the third control portion is adapted to store, as the third reference value, the third detection signal generated by the third light-receiving portion when the third interface portion receives a user's third setting operation.

19. The optical beam pointing system according to claim 18, wherein, the third light-projecting portion is adapted to project the third visible light beam traveling vertically in the shape of a cross consisting of a traversal beam spreading along the line connecting the first optical beam pointer and the second optical beam pointer, and a longitudinal beam spreading perpendicular to the traversal beam, the longitudinal beam is converted by the beam splitter into a third horizontal beam spreading horizontally, the third horizontal beam forming a part of the fractional light beam, the traversal beam is converted by the beam splitter into a third vertical beam spreading vertically, the third vertical beam forming the other part of the fractional light beam, the third optical beam pointer further includes a optical element for converting the third horizontal beam into a fourth vertical beam spreading vertically by rotating spread directions of the third horizontal beam by 90°, and the third light-receiving portion consists of two third optical receivers, one for receiving the third vertical beam, the other for receiving the fourth vertical beam.

20. The optical beam pointing system according to claim 18, wherein each signal is wirelessly received/transmitted between the third transmitting portion and the third receiving portion.

21. The optical beam pointing system according to claim 16, further comprising:

a third optical beam pointer disposed above the irradiation center; and an optical beam monitoring device disposed laterally to the third optical beam pointer, wherein, the third optical beam pointer includes:
  a third light-projecting portion for projecting a third visible light beam aimed at the irradiation center; and
  a beam splitter for generating a fractional light beam from the third visible light beam, the fractional light beam traveling toward the optical beam monitoring device, the optical beam monitoring device includes:
  a third light-receiving portion for receiving the fractional light beam and generating a third detection signal in accordance with a receiving position at which the fractional light beam is received; and
  a third transmitting portion for transmitting the third detection signal to the third optical beam pointer, and the third optical beam pointer includes:
  a third receiving portion for receiving the third detection signal from the third transmitting portion;
  a third control portion having previously stored therein, as a third reference value, a value for the third detection signal to be generated by the third light-receiving portion which has received the fractional light beam derived from the third visible light beam passing through the irradiation center as aimed, the third control portion generating a third correction signal for correcting a projection angle of the third light-projecting portion when a difference between the third reference value and a value for the third detection signal received by the third receiving portion falls outside a tolerable range; and a third actuator for correcting a projection angle of the third light-projecting portion in accordance with the third correction signal, such that the third visible light beam passes through the irradiation center.

22. The optical beam pointing system according to claim 21, wherein, the optical beam monitoring device further includes:
a third interface portion; and
a fourth control portion electrically connected to at least the third interface portion and the third transmitting portion,
the fourth control portion transmits a third instruction signal to the third receiving portion via the third transmitting portion when the third interface portion receives a user's third setting operation, and
the third control portion is adapted to store, as the third reference value, the third detection signal received by the third receiving portion when the third control portion receives the third instruction signal via the third receiving portion.

23. The optical beam pointing system according to claim 22, wherein, the third light-projecting portion is adapted to project the third visible light beam traveling vertically in the shape of a cross consisting of a traversal beam spreading along the line connecting the first optical beam pointer and the second optical beam pointer, and a longitudinal beam spreading perpendicular to the traversal beam,
the longitudinal beam is converted by the beam splitter into a third horizontal beam spreading horizontally, the third horizontal beam forming a part of the fractional light beam,
the traversal beam is converted by the beam splitter into a third vertical beam spreading vertically, the third vertical beam forming the other part of the fractional light beam,
the third optical beam pointer further includes a optical element for converting the third horizontal beam into a fourth vertical beam spreading vertically by rotating spread directions of the third horizontal beam by 90°, and
the third light-receiving portion consists of two third optical receivers, one for receiving the third vertical beam, the other for receiving the fourth vertical beam.

24. The optical beam pointing system according to claim 22, wherein each signal is wirelessly received/transmitted between the third transmitting portion and the third receiving portion.

* * * * *